US005980907A

United States Patent [19]

Dougan et al.

[11] Patent Number: 5,980,907
[45] Date of Patent: *Nov. 9, 1999

[54] VACCINES CONTAINING BACTERIA ATTENUATED BY MUTATION OF THE HTRA GENE

[75] Inventors: Gordan Dougan; Ian George Charles, both of Beckenham; Carlos Estenio Hormaeche; Kevin Stuart Johnson, both of Cambridge; Steven Neville Chatfield, Beckenham, all of United Kingdom

[73] Assignee: Glaxo Wellcome Inc., Research Triangle Park, N.C.

[*] Notice: This patent is subject to a terminal disclaimer.

[21] Appl. No.: 08/463,875

[22] Filed: Jun. 5, 1995

Related U.S. Application Data

[62] Continuation of application No. 08/350,741, Dec. 7, 1994, Pat. No. 5,804,194, which is a continuation of application No. 08/239,910, May 9, 1994, abandoned, which is a continuation of application No. 07/952,737, filed as application No. PCT/GB91/00484, Mar. 28, 1991, abandoned.

[30] Foreign Application Priority Data

Mar. 30, 1990 [GB] United Kingdom .................. 9007194

[51] Int. Cl.$^6$ .......................... A61K 39/02; A61K 39/10; A61K 39/102; A01N 63/00
[52] U.S. Cl. ................... 424/200.1; 424/93.2; 424/93.4; 424/235.1; 424/253.1; 424/254.1; 424/256.1; 424/257.1; 424/258.1; 424/261.1; 424/826
[58] Field of Search ............................. 424/235.1, 258.1, 424/93.4, 93.2, 200.1, 826, 257.1, 256.1, 261.1, 253.1, 254.1

[56] References Cited

U.S. PATENT DOCUMENTS 4,895,717  1/1990  Witter .
5,114,844  5/1992  Cohen .

FOREIGN PATENT DOCUMENTS 0127153  5/1984  European Pat. Off. .
0184086  11/1985  European Pat. Off. .
0322237  12/1988  European Pat. Off. .
0400958  12/1990  European Pat. Off. .
WO 80/02504  11/1980  WIPO .
WO 88/05821  8/1988  WIPO .

OTHER PUBLICATIONS

Lazar et al. Mol. Cell Biology 8(3):1247–1252, 1988.
Burgess et al. J. Cell Biology 111:2129–37, 1990.
Elsinghorst et al., "Molecular Cloning of Epithelial Cell Invasion Determinants from Enterotoxigenic *Escherichia coli*", Infection and Immunity 60(6):2409–2417 (1992).
Weel et al, "In Situ Expression and Localization of *Neisseria gonorhoeae* Opacity Proteins in Infected Epithelial Cells: Apparent Role of Opa Proteins in Cellular Invasion", J. Exp. Med. 173:1395–1405 (1991).
Donnenberg et al, "Epithelial Cell Invasion: An Overlooked Property of Enteropathogenic *Escherichia coli* (EPEC) Associated with the EPEC Adherence Factor", The Journal of Infectious Diseases 160(3):452–459 (1989).
Simon et al, "*Escherichia coli* expressing a *Neisseria gonorrhoeae* opacity–associated outer membrane protein invade human cervical and endometrial epithelial cell lines", Proc. Natl. Acad. Sci. USA 89:5512–5516 (1992).
Arko et al, "Binding of S Protein by *Neisseria gonorrhoeae* and Potential Role in Invasion", Journal of Clinical Microbiology 29:70–75 (1991).
Ewanowich et al, "Phorbol Myristate Acetate Inhibits HeLa 229 Invasion by *Bordetella pertussis* and Other Invasive Bacterial Pathogens", Infection and Immunology 58(10):3187–3193 (1990).
Ewanowich et al, "Invasion of HeLa 229 Cells by Virulent *Bordetella pertussis*", Infection and Immunity 57(9):2698–2704 (1989).
I. Miller et al, Infection and Immunity 57, No. 9, 1989 2758–2763.
B. Lipinska et al, J. Bacteriology 171, No. 3, 1989, 1574–1584.
B. Bukau, J. Bacteriology, 171, No. 5, 1989, 2337–2346.
Kusukawa et al, Genes and Development 2, 1988, 874–882.
N. Kusukawa et al, The EMBO Journal, 8, No. 11, 1989, 3517–3521.
Groisman et al, Proc. Natl. Acad. Sci., 86, 1989, 7077–7081.
J.W. Foster et al, J. Bacteriology, 172, No. 2, 1990, 771–778.
S.N. Chatfield et al, Vaccine 7, No. 6, 1989, 495–498.
K. Johnson et al, Biological Abstracts, 91, Abstract 119974 & Mol. Microbiol 5 (2), 1991, 401–408.
Bacon et al, Br.J.Exp. Path 31, 714–724 (1950).
Roy Curtiss III et al, Vaccine 6, 155–160 (1988).
Dorman et al, Infec. Immun. 57, 2136–2140 (1989).
Fields et al, Science 243, 1059–1062 (1989).
Niedhardt et al, Cell. and Mol. Biol. 1334–1345 (1987).
Lipinska et al, Nuc. Acids. Res 21, 10053–67 (1988).
Strauch et al, Proc. Natl. Acad. Sci. 85, 1576–1580 (1988).
Maniol et al, Proc. Natl. Acad. Sci. 82, 8129–8133 (1985).
Ronson et al, Cell, 49, 579–581 (1987).
Buck et al, Nature, 320, 374–378 (1986).
Hirschman et al, Proc. Natl. Acad. Sci. 82, 7275 (1985).
Nixon et al, Proc. Natl. Acad. Sci. 83, 7850–7854 (1986).
Reitzer et al, Cell. 45, 785 (1986).
Makino et al, J.Mol. Biol. 192, 549–556 (1986).
Albin et al, J. Biol. Chem. 261, 4698 (1986).

(List continued on next page.)

Primary Examiner—Anthony C. Caputa
Assistant Examiner—Mark Navarro
Attorney, Agent, or Firm—Nixon & Vanderhye P.C.

[57] ABSTRACT

Attenuated microorganism for use in immunoprophylaxis in which the attenuation is brought about by the presence of a mutation in the DNA sequence of the microorganism which encodes, or which regulates the expression of DNA encoding a protein that is produced in response to environmental stress, the microorganism optionally being capable of expressing DNA encoding a heterologous antigen.

17 Claims, 4 Drawing Sheets

OTHER PUBLICATIONS

Drury et al, J. Biol. Chem. 260, 4236–4272 (1985).
Ronson et al, J. Bacteriol, 169, 2424 (1987).
Winans et al, Proc. Natl. Acad. Sci. 83, 8278 (1986).
Arico et al, Proc. Natl. Acad. Sci. 86, 6671–6675 (1989).
Clements et al, Infec. and Immun. 46, 2, 564–569 (1984).
Formal et al, Infec. and Immun. 34, 746–750 (1981).
Chatfield et al, Microb. Pathog. 12:145–151 (1992).
"*E. coli* and *Salmonella Typhimurium*", Cellular and Molecular Biology, Neidhardt et al (Ed) published in 1987, see pp. 378–380.
Hone et al, "Construction of genetically defined double aro mutants of *Salmonella typhi*", Vaccine 9:810–816 (1991).
Tacket et al. "Comparison of the Safety and Immunogenicity of ΔaroC ΔaroD and Δcya Δcrp *Salmonella typhi* Strains in Adult Volunteers", Infection and Immunity 60:536–541 (1992).
Tacket et al, "Clinical acceptability and immunogenicity of CVD 908 *Salmonella typhi* vaccine strain", Vaccine 10:443–446 (1992).
Collins, "Vaccines and Cell–Mediated Immunity", Bacteriological Reviews 38:371–402 (1974).

O'Callaghan et al, "Characterization of Aromatic–and Purine–Dependent *Salmonella typhimurium:* Attenuation, Persistence, and Ability to Induce Protective Immunity in BALB/c Mice", Infection and Immunity 56:419–423 (1988).

Jones et al, "Oral vaccination of calves against experimental salmonellosis using a double aro mutant of *Salmonella typhimurium*", Vaccine 9:29–34 (1991).

Miller et al, "Bacteriophage P22 as a vehicle for transducing cosmid gene banks between smooth strains of *Salmonella typhimurium:* Use in identifying a role for iroD in attenuating virulent Salmonella strains", Mol. Gen. Genet. 215:312–316 (1989).

Dougan et al, "Construction and Characterization of Vaccine Strains of Salmonella Harboring Mutations in Two Different aro Genes", The Journal of Infectious Diseases 158(6):1329–1335 (1988).

Sanderson et al, *Escherichia Coli* and *Salmonella Typhimurium,* 2:877–918 published in 1987 by American Society of Microbiology.

```
                                                                                    288
  . G . G . N . I . G . I . G . F . A . I . P . S . N . M . V . K . N . L . T . S . Q . M . V . E . Y . G . Q . V . K . R       289
CGGGGGCAACATCGGTATCGGCTTCGCTATCCCCAGTAACATGGTGAAAAACCTGACGTCGCAGATGGTGGAATACGGCCAGGTGAAACG                                    1260

318
  . G . E . L . G . I . M . G . T . E . L . N . S . E . L . A . K . A . M . K . V . D . A . Q . R . G . A . F . V . S . Q       319
CGGCGAACTGGGGATCATGGGGACTGAGCTGAATTCCGAATTGGCGAAAGCGATGAAAGTCGACGCCCAGCGAGGCGGTTCGTCAGCCA                                    1350

348
  . V . M . P . N . S . S . A . A . K . A . G . I . K . A . G . D . V . I . T . S . L . N . G . K . P . I . S . S . F . A       349
GGTGATGCCGAATTCGTCCGCGGGCGAAAGCGGGTATCAAAGCGGGGATGTCATTACCTCGCTGAACGGTAAACCGATCAGCAGCTTTGC                                    1440

378
  . A . L . R . A . Q . V . G . T . M . P . V . G . S . K . I . S . L . G . L . L . R . E . G . K . A . I . T . V . N . L       379
GGCGCTGCGCGCTCAGGTCGGCACTATGCCCGGTCGGCAGCAAATCAGCCTCGGTCTGCTGCGTGAAGGTAAAGCGATTACGGTGAATCT                                    1530

408
  . E . L . Q . Q . S . Q . S . Q . V . D . S . S . T . I . F . S . G . I . E . G . A . E . M . S . N . K . G . Q . D       409
GGAACTGCAGCAGAGCAGCCAGAGTCAGGTTGATTCCAGCACCATCTTCAGCGGGATTGAAGGCGCTGAAATGAGCAATAAAGGCCAGGA                                    1620

438
  . Q . K . G . V . V . S . S . V . K . A . N . S . P . A . A . Q . I . G . L . K . K . G . D . V . I . I . G . A . N . Q       439
TAAAGGCGGTTGTGTGAGCAGCGTGAAAGCGAACTCACCCGCCGCGCAAATTGGCCTCAAAAAAGGCGATGTGATTATCGGCGCTAACCA                                    1710

468
  . A . D . P . V . K . N . I . A . E . L . R . K . I . L . D . S . K . P . S . V . L . A . L . N . I . Q . R . G . D . S       469
GCAGCCGGTGAAAAATATCGCCGAGCTGCGTAAGATTCTCGACAGCAAGCCGTCGGTTCTGGCGCTGAATATTCAGCGTGGTGATAGTTC                                    1800

492
  . L . P . V . N . A . V . I . S . L . N . P . F . L . K . T . G . R . G . S . P . Y . N . L . *                              475
  . I . Y . L . L . M . Q . *                                                                                                   1890
TATTTATTTGCTGATGCAGTAATCACCTTTGTCATTTGCACAATGTCGAGACCTGTCATCTTCCTTATGCTTGTGCTCTGCTCACAGGAGGGATTTATGGCT

1980
CTTATTTGCACCGTTTGTGTCATTGCACAATGTCGAGACCTGTCATCTTCCTTATGCTTGTGCTCTGCTCACAGGAGGGATTTATGGCT
```

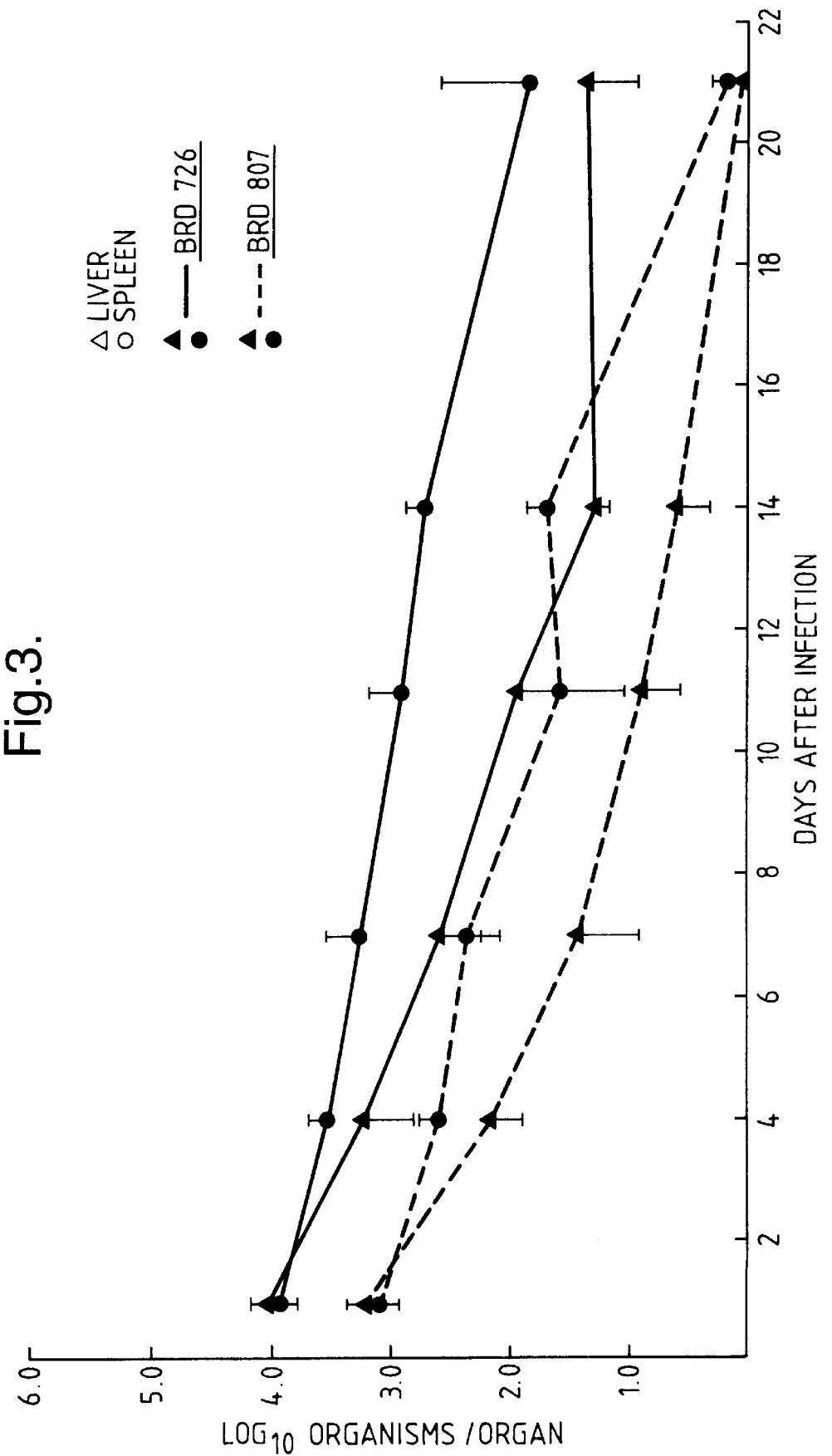

VACCINES CONTAINING BACTERIA ATTENUATED BY MUTATION OF THE HTRA GENE

RELATED APPLICATIONS

This is a continuation of application Ser. No. 08/350,741, filed Dec. 7, 1994, now U.S. Pat. No. 5,804,194; which is a continuation of application Ser. No. 08/239,910, filed May 9, 1994, now abandoned; which is a continuation of application Ser. No. 07/952,737, filed Nov. 30, 1992, now abandoned; which is the U.S. national phase of PCT/GB91/00484, filed Mar. 28, 1991.

DESCRIPTION OF THE PRIOR ART

The principle behind vaccination or immunoprophylaxis is to induce an immune response in an animal to a pathogenic organism by innoculation with an attenuated strain of the organism thus providing protection against subsequent challenge. In 1950 Bacon et al (Br.J.Exp.Path. 31, 714–724) demonstrated that certain auxotrophic mutants of *S.typhi* were attenuated in mice when compared to the parental strain. Certain of these auxotrophic mutants have been proposed as being suitable candidates for the basis of a whole cell vaccine. (See for example Hosieth and Stocker, *Nature*, 1981 241, 238–239, and European patent publication 322, 237). In addition to mutations in an essential auxotrophic pathway, other loci have been identified where mutations result in attenuation of microorganisms. Examples of such loci include regulons that exert pleiotropic effects, e.g., the cya/crp system (Roy Curtiss III et al, *Vaccine* 6, 155–160, 1988) and the ompR envZ system (Dorman et al, *Infect. Immun.* 57, 2136–2140, 1989) and the phoP system (Fields et al, *Science* 243, 1059–1062, 1989).

In many microorganisms, between one and two dozen proteins are produced in response to a range of different environmental stresses, such as high temperature, nutrient deprivation, toxic oxygen radicals and metabolic disruption. These represent part of the coordinated regulation of various different genes induced in response to the particular stress to which the microorganism is subjected. The family of major stress proteins (also known as heat shock proteins) is amongst the most highly conserved in nature. Substantial homology exists amongst members of this family isolated from *E.coli, Drosophilia* spp. and man (for a recent review see Neidhardt, G. C. & Van Bogelen, R. A. (1987) *Escherichia coli* and *Salmonella typhimurium:* Cellular and Molecular Biology. F. C. Neidhardt et al. eds. pp. 1334–1345. American Society for Microbiology, Washington D.C.). For example: Hsp90, Hsp70 and Hsp60 are heat shock proteins found in all prokaryotes and eukaryotes. Amino acid sequence comparison between Hsp90 from *E.coli* and that from man shows that approximately half the amino acid residues are identical. Other members of the stress protein family are GrpE, GroEL, DnaK, GroES, Lon and DnaJ.

The genes encoding the family of heat shock proteins are transcribed by RNA polymerase co-operating with the $\sigma^{32}$ factor, the product of the rpoH gene (reviewed by Neidhardt, F. C. and van Bogelen, R. A., 1987. In *Escherichia coli* and *Salmonella typhimurium:* Cellular and Molecular Biology, Neidhardt, F. C. et al eds. pp. 1334–1345, American Society for Microbiology, Washington, D.C.). Recently, Lipinska et al (*Nucleic.Acids.Res.* 1988 21, 10053–10067) have described a heat shock protein in *E.coli*, referred to as HtrA, that appears to be $\sigma^{32}$-independent. Examination of the promoter region of the htrA gene shows DNA sequence homology with the P.3 promoter of the rpoH gene; a promoter known to be recognised by $\sigma^{E}(\sigma^{24})$ factor. This similarity suggests that the htrA promoter may also be recognised by the RNA polymerase-$\sigma^{E}(\sigma^{24})$holoenzyme.

Phenotypically, in *E.coli*, a mutation in the htrA locus abolishes the ability of bacterium to survive at temperatures above 42° C. (Lipinska et al, 1989, *J.Bacteriol*, 171, 1574–1584). The gene maps at 4 min on the *E.coli* chromosome and encodes a protein with a relative molecular mass (Mr) of 51,163. This protein precursor undergoes N-terminal processing involving the removal of a signal peptide sequence (Lipinska et al, 1988, *Nucleic.Acids.Res.* 21, 10053–10067), to yield the mature form of the polypeptide upon secretion through the inner membrane of the bacterium. Independently, the htrA gene has been identified as degP by Strauch, K. L. and Beckwith, J. 1988 (*Proc.Natl.Acad.Sci.* U.S.A. 85, 1576–1580) who were examining *E.coli* mutants with decreased protease activity, degP mutants were isolated by TnphoA mutagenesis (Manoil, C. & Beckwith, J. 1985, *Proc.Natl.Acad.Sci.* U.S.A. 82, 8129–8133) and were recognised by the increased stability of a hybrid Tsr-phoA (Tsr-AP2) recombinant protein in a degP background (Strauch, K. L. and Beckwith, J. 1988. *Proc.Natl. Acad.Sci.* U.S.A. 85, 1576–1680). In *E.coli* the genes identified as degP and htrA appear to be identical and encode a protein that is a member of the 'stress-response' family.

DESCRIPTION OF THE INVENTION

The present invention provides an attenuated microorganism for use in immunoprophylaxis in which the attenuation is brought about by the presence of a mutation in the DNA of the microorganism which encodes, or which regulates the expression of DNA encoding, a protein that is produced in response to environmental stress, the microorganism optionally being capable of expressing DNA encoding a heterologous antigen.

The microorganisms for use with the present invention are preferably bacteria especially Gram-negative bacteria which invade and grow within eucaryotic cells and colonise the muscosal surface. Examples of these include members of the genera Salmonella, Bordetella, Vibrio, Haemophilus and Escherichia. In particular the following species can be mentioned: *S.typhi*—the cause of human typhoid; *S.typhimurium*—the cause of salmonellosis in several animal species; *S.enteritidis*—a cause of food poisoning in humans; *S.choleraesuis*—the cause of salmonellosis in pigs; *Bordetella pertussis*—the cause of whooping cough; *Haemophilus influenzae*—a cause of meningitis; and *Neisseria gonorrhoeae*—the cause of gonorrhoea.

The mutation of the DNA is a non-reverting mutation, namely one which cannot be repaired in a single step. Genetic mutations of this sort include deletion, inversion, insertion or substitution mutations. Deletion mutations can be generated using transposons. These are DNA sequences comprising from between 750 to thousands of base pairs which can integrate into the host's chromosomal DNA. The continuity of the DNA sequence of interest is thus disrupted with the loss of gene function. Transposons can be deleted from the host chromosomal DNA; most frequently excision is imprecise leading to a non-reverting mutation. Substitution or insertion mutations can arise by use of an inactivated DNA sequence carried on a vector which recombines with or crosses-over with the DNA sequence of interest in the host's chromosomal DNA with the consequent loss of gene function.

Examples of proteins that are produced in response to environmental stress include heat shock proteins (which are produced in response to a temperature increase above 42° C.); nutrient deprivation proteins (which are produced in response to levels of essential nutrients such as phosphates or nitrogen which are below that which the microorganism requires to survive); toxic stress proteins (which are produced in response to toxic compounds such as dyes, acids or possibly plant exudates); or metabolic disruption proteins (which are produced in response to fluctuations in for example ion levels affecting the microorganisms ability to osmoregulate, or vitamin or co-factor levels such as to disrupt metabolism).

Preferably a heat shock protein is the one encoded by the htrA gene as set out in FIG. 1. (SEQ ID No: 1) (also characterised as degP). Other proteins are encoded by genes known to be involved in the stress response such as grpE, groEL, (moPA), dnaK, groES, Ion and dnaJ. There are many other proteins encoded by genes which are known to be induced in response to environmental stress (Ronson et al, Cell 49, 579–581). Amongst these the following can be mentioned: the ntrB/ntrC system of E.coli, which is induced in response to nitrogen deprivation and positively regulates glnA and nifLA (Buck et al., Nature 320, 374–378, 1986; Hirschman et al., Proc.Natl.Acad.Sci. U.S.A., 82, 7525, 1985; Nixon et al., Proc.Natl.Acad.Sci. U.S.A. 83, 7850–7854, 1986, Reitzer and Magansanik, Cell, 45, 785, 1986); the phoR/phoB system of E.coli which is induced in response to phosphate deprivation (Makino et al., J.Mol.Biol. 192, 549–556, 1986b); the cpxA/sfrA system of E.coli which is induced in response to dyes and other toxic compounds (Albin et al., J.Biol.Chem. 261 4698, 1986; Drury et al., J.Biol.Chem. 260, 4236–4272, 1985). An analogous system in Rhizobium is dctB/dctD, which is responsive to 4C-discarboxylic acids (Ronson et al., J.Bacteriol. 169, 2424 and Cell 49, 579–581, 1987). A virulence system of this type has been described in Agrobacterium. This is the virA/virG system, which is induced in response to plant exudates (le Roux et al., EMBO J. 6, 849–856, 1987; Stachel and Zambryski., Am.J.Vet.Res. 45, 59–66, 1986; Winans et al., Proc.Natl. Acad.Sci. U.S.A., 83, 8278, 1986). Similarly the bvgC-bvgA system in Bordetella pertussis (previously known as vir) regulates the production of virulence determinants in response to fluctuations in Mg2+ and nicotinic acid levels (Arico et al, 1989, Proc.Natl.Acad.Sci. U.S.A. 86, 6671–6675).

For use in the form of a live vaccine, it is clearly important that the attenuated microorganism of the present invention does not revert back to the virulent state. The probability of this happening with a mutation in a single DNA sequence is considered to be small. However, the risk of reversion occurring with a microorganism attenuated by the presence of mutations in each of two discrete DNA sequences, is considered to be insignificant. It is preferred therefore that the attenuation of the microorganism of the present invention is brought about by the presence of a mutation in the DNA sequence which encodes, or which regulates the expression of DNA encoding, a protein that is produced in response to environmental stress and by the presence of a mutation in a second DNA sequence. For bacteria, the second DNA sequence preferably encodes an enzyme involved in an essential auxotrophic pathway or is a sequence whose product controls the regulation of osmotically responsive genes, i.e. ompR, (Infect and Immun 1989 2136–2140). Most preferably, the mutation is in a DNA sequence involved in the aromatic amino acid biosynthetic pathway, more particularly the DNA sequences encoding aroA, aroC or aroD. (EP Publication Number 322237).

The attenuated microorganisms of the present invention are constructed by the introduction of a mutation into the DNA sequence by methods known to those skilled in the art (Maniatis, Molecular Cloning and Laboratory Manual, 1982). Non-reverting mutations can be generated by introducing a hybrid transposon TnphoA into, for example, s.typhimurium strains. TnphoA can generate enzymatically active protein fusions of alkaline phosphatase to periplasmic or membrane proteins. The TnphoA transposon carries a gene encoding kanamycin resistance. Transductants are selected that are kanamycin resistant by growing colonies on an appropriate selection medium.

Alternative methods include cloning the DNA sequence into a vector, eg. a plasmid or cosmid, inserting a selectable marker gene into the cloned DNA sequence, resulting in its inactivation. A plasmid carrying the inactivated DNA sequence and a different selectable marker can be introduced into the organism by known techniques (Maniatis, Molecular Cloning and Laboratory Manual, 1982). It is then possible by suitable selection to identify a mutant wherein the inactivated DNA sequence has recombined into the chromosome of the microorganism and the wild-type DNA sequence has been rendered non-functional in a process known as allelic exchange. In particular, the vector used is preferably unstable in the microorganism and will be spontaneously lost. The mutated DNA sequence on the plasmid and the wild-type DNA sequence may be exchanged by a genetic cross-over event. Additional methods eliminate the introduction of foreign DNA into vaccine strains at the site of mutations.

The invention therefore provides a process for the production of an attenuated microorganism according to the invention which comprises introduction of a mutation in the DNA sequence of the microorganism which encodes, or which regulates expression of a DNA sequence encoding, a protein that is produced in response to environmental stress, by either a) transposon mutagenesis; or b) transforming the microorganism with a vector incorporating a DNA sequence encoding, or regulating the expression of a DNA sequence encoding, a protein that is produced in response to environmental stress and which contains a non-reverting mutation; and screening to select the desired microorganisms.

The attenuated microorganism of the present invention is optionally capable of expressing a heterologous antigen. This expression is likely to be more favourable in htrA mutants because of the increased stability of recombinant antigens associated with the degP phenotype. Such antigens may be viral, bacterial, protozoal or of higher parasitic microorganisms. Such microorganisms may then form the basis of a bi- or multi-valent vaccine. Examples of useful antigens include E.coli heat labile toxin B subunit (LT-B), E.coli K88 antigens, FMDV (Foot and Mouth) peptides, Influenza viral proteins, P.69 protein from B.pertussis. Other antigens which could be usefully expressed would be those from Chlamydia, flukes, mycoplasma, roundworms, tapeworms, rabies virus and rotavirus.

A microorganism capable of expressing DNA encoding a heterologous antigen may be produced by transformation of the microorganism with an expression cassette. Expression cassettes will include DNA sequences, in addition to that coding for the heterologous antigen, which will encode transcriptional and translational initiation and termination sequences. The expression cassette may also include regulatory sequences. Such expression cassettes are well known in the art and it is well within the ability of the skilled man to construct them. The expression cassette may form part of a vector construct or a naturally occurring plasmid. An example of a genetically engineered attenuated Salmonella which is capable of expressing a heterologous antigen is described in EP publication 127,153. The expression cassette may also be engineered to allow the incorporation of the heterologous gene into the chromosome of the microorganism.

A further bivalent vaccine comprising an attenuated *Salmonella typhi*, capable of expressing the *E.coli* heat-labile enterotoxin subunit B is disclosed by Clements et al (Infection ad Immunity, 46, No.2. 1984, 564–569). Ty21a, an attenuated *S.typhi* strain, has been used to express other antigens such as the *Shigella sonnei* form I antigen (Formal et al., Infection and Immunity, 34, 746–750, 1981).

According to a further aspect of the invention there is provided a vaccine which comprises an effective amount of an attenuated microorganism, preferably a bacterium, as herein described and a pharmaceutically acceptable carrier.

The vaccine is advantageously presented in a lyophilised form, for example in a capsular form, for oral administration to a patient. Such capsules may be provided with an enteric coating comprising for example EUDRAGATE "S", EUDRAGATE "L" Cellulose acetate, cellulose pthalate or hydroxy propylmethyl cellulose. These capsules may be used as such, or alternatively, the lyophilised material may be reconstituted prior to administration, eg. as a suspension. Reconstitution is advantageously effected in a buffer at a suitable pH to ensure the viability of the organisms. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramammary.

The present invention also provides a method of prophylactic treatment of a host (particularly a human host) with an infection caused by a microorganism which comprises administering to said host an effective dose of a vaccine according to the invention. The dosage employed in such a method of treatment will be dependent on various clinical factors, including the size and weight of the host, the type of vaccine formulated. However, for attenuated *S.typhi* a dosage comprising the administration of $10^9$ to $10^{11}$ *S.typhi* organisms per dose is generally convenient for a 70 kg adult human host.

The following examples provide experimental details in accordance with the present invention. It will be understood that these examples are not intended to limit the invention in any way.

BRIEF DESCRIPTION OF THE DRAWINGS

FIGS. 1A and 1B. DNA sequence of the htrA gene and the amino acid sequence of the protein it encodes (SEQ ID NO:1 corresponds to the DNA sequence of FIG. 1, SEQ ID NO:2 corresponds to the lower of the two amino acid sequences in FIG. 1 and SEQ ID NO:3 corresponds to the upper of the amino acid sequences in FIG. 1).

EXAMPLE 1

Figure 2:
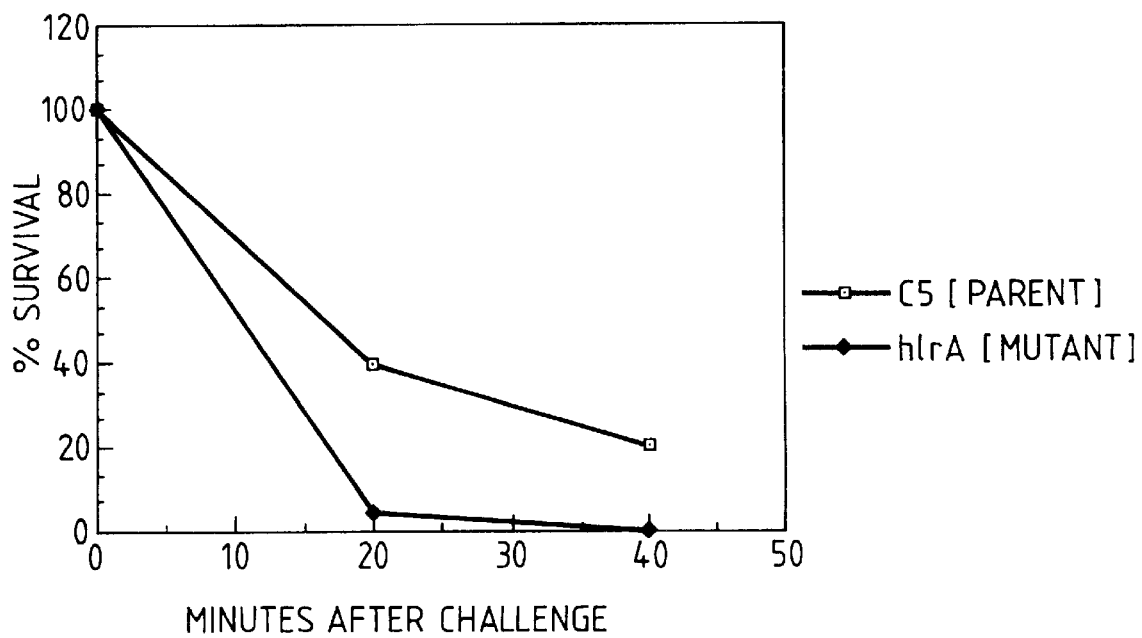
FIG. 2. Sensitivity of *S.typhimurium* htrA mutant 046 to temperatures above 42° C. and oxygen radicals FIG. 3. In vivo kinetics of *S.typhimurium* strains harbouring a mutation in htrA (BRD726) and htrA aro mutations (BRD807).

Identification of the htrA gene in *Salmonella typhimurium* and generation of an htrA mutant.

Figure 1A:
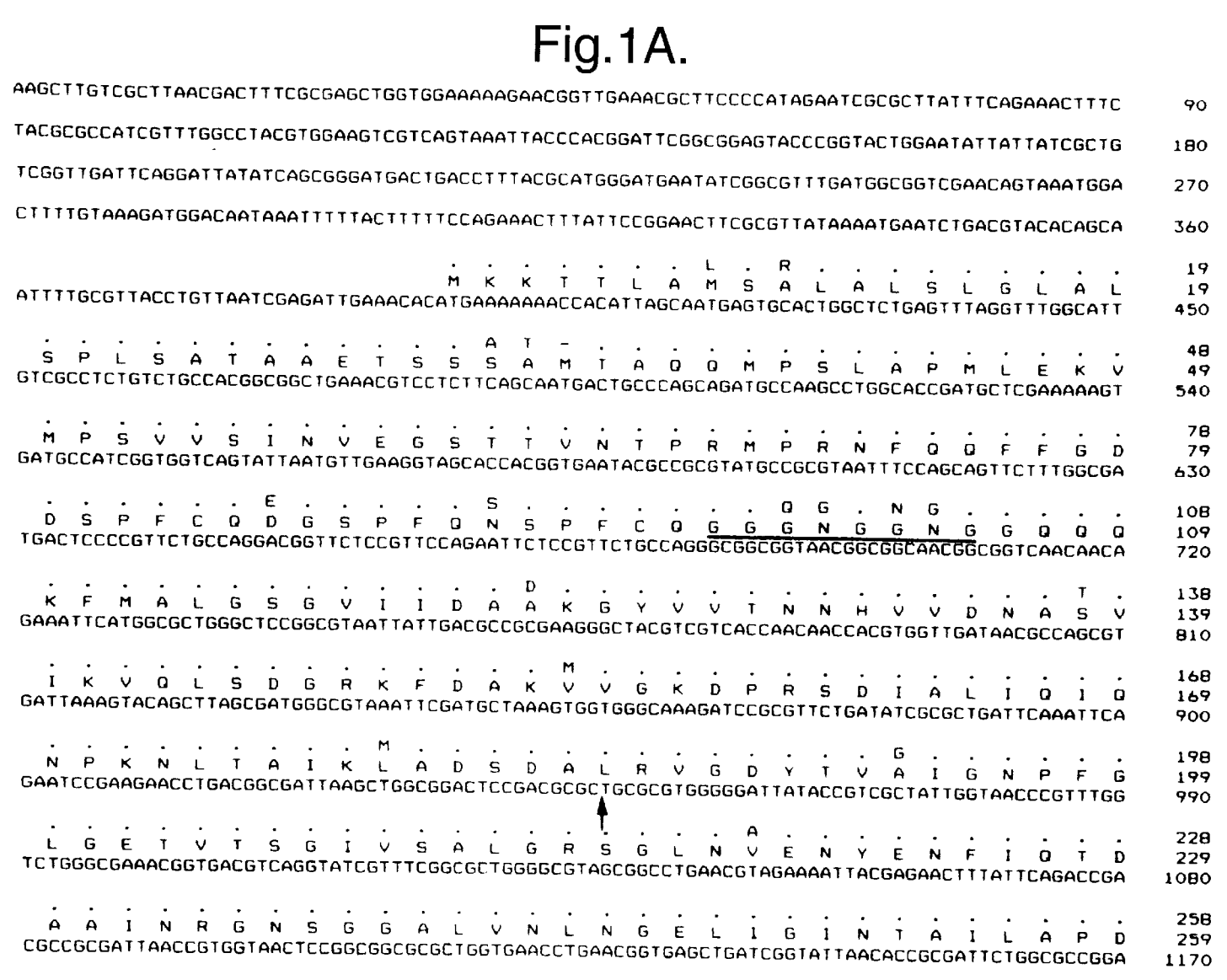

TnphoA mutagenesis was used in the mouse virulent *Salmonella typhimurium* strain C5 (Miller et al, 1989, Infect.Immunol, 57, 2758–2763). Mutants were selected likely to harbour lesions in genes that have a signal peptide sequence, i.e. proteins likely to be targeted through a bacterial membrane. Isolation of the DNA flanking the TnphoA insertion identifies the gene that has been insertionally activated. This gene was isolated and its DNA sequence was determined by standard methods (see FIG. 1. SEQ ID No: 1) (Maniatis et al., 1982, In Molecular Cloning: A laboratory manual. Cold Spring Harbour Laboratory, Cold Spring Harbour, N.Y.; Sanger et al., 1977, Proc.Natl.Acad.Sci. U.S.A. 74, 5463–5467). Comparison of the translated protein sequence with sequences held in the EMBL Database showed surprisingly that it shared 88% homology with the sequence of the htrA product from *E.coli* (FIG.1. SEQ ID No: 1).

EXAMPLE 2

Identification of htrA in *S.typhimurium* as a gene involved in the stress-response

*E.Coli* mutants harbouring lesions in the htrA gene are unable to grow at temperatures above 42° C. The *S.typhimurium* htrA mutant, 046, was tested for growth at elevated temperatures and was found to grow as well as the present strain C5. However, when tested for sensitivity to oxygen radicals, the mutant 046 showed decreased resistance as compared with the parent C5 strain clearly indicating that the gene is responsible (at least in part) for this aspect of the stress response (see FIG. 2).

EXAMPLE 3

Comparison of attenuated *Salmonella typhimurium* strain 046 with virulent parent strain *Salmonella typhimurium* C5.

The attenuated strains were constructed using TnphoA transposon mutagenesis as described previously (Miller et al., 1989, Infect. Immun. 57, 2758–2763).

After oral administration the mutant strain 046 had a $Log_{10}$ $LD_{50}$ of greater than 9 cells as compared to the parental strain, C5, which has a $Log_{10}$ $LD_{50}$ of 6.38 cells. (All $LD_{50}$ were calculated after 28 days). Thus 046 is highly attenuated. After i.v. administration 046 had an i.v. $Log_{10}$ $LD_{50}$ of 5.13 cells compared to less than 10 cells for C5 and we again conclude that 046 is highly attenuated compared to C5.

EXAMPLE 4

Protection of mice after oral challenge.

Mice were immunised with 046 and challenged 28 days later with the virulent parental strain C5. Mice vaccinated with using $10^{10}$ cells of 046 showed excellent protection against challenge with C5. eleven weeks after vaccination. The $Log_{10}$ $LD_{50}$ in immunised animals was 9.64 cells compared with 6.6 cells for unimmunised controls. Thus, mice vaccinated orally with a single dose of 046 were well protected against virulent C5 challenge.

EXAMPLE 5

Construction of a defined *S.typhimurium* SL1344 htrA mutant

Sequence data facilitated the identification of suitable restriction endonuclease sites that could be used to introduce a deletion into the htrA gene. A 1.2 Kb deletion was introduced by digesting with EcoRV and religating. A drug resistant marker was also introduced into the gene (Kanamycin cassette, Pharmacia) by standard techniques to enable selection for the presence of the deleted gene. The plasmid harbouring the deleted htrA gene was introduced into a polA strain *S.typhimurium* (BRD207) in which the plasmid cannot replicate. The only way that kanamycin resistance can be maintained in the host is if there has been a recombination event between the *S.typhimurium* sequences on the vector and the homologous regions on the chromosome. Loss of ampicillin resistance while maintaining kanamycin resistance indicates a second homologous recombination event resulting in the replacement of the intact htrA gene with the deleted one. Colonies resistant to kanamycin were isolated and checked for ampicillin resistance. One colony that was kanamycin resistant and ampicillin sensitive was selected for further study and was designated BRD698 (deposited at PHLS, NCTC, 61 Colindale Avenue, London NW9 5HT under Accession No. NCTC 12457 on Mar. 22, 1991 in accordance with the terms of the Budapest Treaty). A P22 lysate was prepared on this strain by standard techniques (Dougan et al, J.Infect.Dis. 158, 1329–1335, 1988) and used to infect SL1344. Kanamycin resistant colonies were isolated and checked for the presence of the deletion by Southern hybridisation. One strain, designated BRD726 (deposited at PHLS under Accession No. NCTC 12458 on Mar. 22, 1991 in accordance with the terms of the Budapest Treaty) was selected for further study.

EXAMPLE 6

Construction of an *S.typhimurium* SL1344 aroA htrA double mutant

The P22 lysate prepared on BRD698 was used to introduce the htrA deletion into an *S.typhimurium* SL1344 strain already harbouring a deletion in aroA. The method for introducing an aroA deletion has already been described by Dougan et al, J.Infect.Dis. 158, 1329–1335, 1988. One strain that was found to have deletions in both aroA and htrA was selected for further study and was designated BRD807, (deposited at PHLS under Accession No. NCTC 12459 on Mar. 22, 1991 in accordance with the terms of the Budapest Treaty).

EXAMPLE 7

Comparison of the attenuation of SL1344 htrA (BRD726) and SL1344 htrA and aroA (BRD807) with the virulent parent strain SL1344

After oral administration BRD726 and BRD807 had $Log_{10}$ $LD_{50}$s of >10.0 cells compared to the virulent parent strain which has a $Log_{10}$ $LD_{50}$ of 6.8 cells*. Both strains were therefore highly attenuated compared to the virulent parent strain SL1344.

*all $LD_{50}$s were calculated after 28 days.

EXAMPLE 8

Assessment of oral vaccine potential of BRD726 and BRD807

BALB/c mice were orally immunised with approximately $10^{10}$ cells of BRD726 and BRD807 as previously described (Dougan et al, J.Infect.Dis. 158, 1329–1335, 1988) and challenged 4 and 10 weeks later with the virulent parent strain SL1344. $LD_{50}$s were calculated by the method of Reed and Muench (Am.J.Hyg. 27, 493–497, 1934). All determinations were carried out at least twice. Mice vaccinated with BRD726 and BRD807 showed excellent protection against challenge with SL1344 at 4 weeks, the $log_{10}$ $LD_{50}$s being >10.0 and 9.7 cells respectively. This compares with log 6.1 cells for unimmunised controls. At 10 weeks $log_{10}$ $LD_{50}$s for BRD726 and BRD807 were 9.11 and 8.11 cells compared to 6.5 for SL1344. Thus the mice immunised with BRD726 had excellent long term immunity to virulent SL1344 challenge. This compares favourably with protection elicited by double aro mutants of SL1344 (Dougan et al, J.Infect.Dis. 158, 1329–1335, 1988). The long term protection afforded by vaccination with BRD807 is 46-fold better than unimmunised controls. Thus both BRD726 and BRD807 make good vaccine strains for BALB/c mice.

EXAMPLE 9

In vivo kinetics of BRD726 and BRD807 in BALB/c mice

The ability of BRD726 and BRD807 to grow in vivo after intravenous administration was assessed. Mice were infected with approximately $10^5$ organisms. Numbers of bacteria in livers and spleens were enumerated at different times during the infection up to 21 days. The results obtained are shown in FIG. 3. Neither BRD726 or BRD807 underwent an initial period of replication in murine tissues. The strains are cleared slowly from the organs and by day 21 BRD807 has almost cleared from the murine tissues while BRD726 is still persisting at low levels.

EXAMPLE 10

Formulation

An attenuated microorganism of the present invention is preferably presented in an oral tablet form.

| INGREDIENT | MG/TABLET |
|---|---|
| Core tablets | |
| 1. Freeze-dried excipient carrier containing $10^9$–$10^{10}$ attenuated bacteria. | 70.0 |
| 2. Silica dioxide (AEROSIL 200) | 0.5 |
| 3. DIPAC (97% sucrose) | 235.0 |
| 4. Cross-linked poly(vinylpryrrolidone) (POVIDONE, KOLLIDON CL) | 7.0 |
| 5. Microcrystalline Cellulose AVICEL PH102 | 35.0 |
| 6. Magnesium Stearate | 2.5 |
| Coating | |
| 7. Opadry Enteric, OY-P-7156 | 35.0 |
| (Polyvinyl acetate phthalate + Diethylphthate) | |
| | 385.0 |

A carrier containing 5% sucrose, 1% sodium glutamate and 1% bacto casitone in an aqueous solvent is prepared. The organisms are suspended in this carrier and then subjected to freeze-drying.

The freeze-dried material is blended with AEROSIL 200 and the blended mixture is sifted through a screen. The sifted powder is mixed with DIPAC (97% sucrose), KOLLIDON CL (poly (vinylpyrrolidone)), AVICEL PH102 (microcrystalline cellulose) and magnesium stearate in a blender. This blend is compressed into tablets for subsequent enteric coatings.

The skilled man will appreciate that many of the ingredients in this formulation could be replaced by functionally equivalent pharmaceutically acceptable excipients.

We claim:

1. A vaccine comprising a prophylactically effective amount of a bacterium and a pharmaceutically acceptable carrier, wherein the bacterium is a Gram-negative bacterium which colonises a mucosal surface and invades and grows within a eukaryotic cell and which is attenuated by non-reverting mutations in the htrA gene and in a second gene.

2. The vaccine as claimed in claim 1, wherein the mutation in the htrA gene is a deletion mutation.

3. The vaccine as claimed in claim 1, wherein the mutation in the htrA gene is an insertion mutation.

4. The vaccine as claimed in claim 1, wherein the bacterium is selected from the group consisting of the genera Salmonella, Bordetella and Escherichia.

5. The vaccine as claimed in claim 1, wherein the mutation in a second gene is in a gene of the aromatic amino acid biosynthetic pathway.

6. The vaccine as claimed in claim 5, wherein the gene of the aromatic amino acid biosynthetic pathway is selected from the group consisting of aroC, aroA and aroD.

7. The vaccine as claimed in claim 1, wherein the bacterium expresses DNA encoding a heterologous antigen.

8. The vaccine as claimed in claim 1 in capsular form.

9. A method of prophylactic treatment of a host for an infection by a Gram-negative bacterium which colonises a mucosal surface and invades and grows within a eukaryotic cell, which comprises administering to said host a prophylactically effective dose of said bacterium in a form attenuated by a non-reverting mutation in the htrA gene.

10. A method of prophylactic treatment of a host for an infection by a microorganism, which comprises administering to said host a prophylactically effective dose of a Gram-negative bacterium which colonises a mucosal surface and invades and grows within a eukaryotic cell, wherein said bacterium is attenuated by a non-reverting mutation in the htrA gene and expresses DNA encoding a heterologous antigen from said microorganism.

11. The method as claimed in claim 9 or 10, wherein the mutation is a deletion mutation.

12. The method as claimed in claim 9 or 10, wherein the mutation is an insertion mutation.

13. The method as claimed in claim 9 or 10, wherein the bacterium is selected from the group consisting of the genera Salmonella, Bordetella, and Escherichia.

14. The method as claimed in claim 9 or 10, in which the attenuated bacterium is further attenuated by a mutation in a second gene.

15. The method as claimed in claim 14, wherein the mutation in a second gene is in a gene of the aromatic amino acid biosynthetic pathway.

16. The method as claimed in claim 15, wherein the gene of the aromatic amino acid biosynthetic pathway is selected from the group consisting of aroC, aroA and aroD.

17. The method as claimed in claim 9 or 10, wherein the bacterium is administered orally.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 1980 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 395..1822
   (xi) SEQUENCE DESCRIPTION: SEQ ID NO: 1:

```
AAGCTTGTCG CTTAACGACT TTCGCGAGCT GGTGGAAAAA GAACGGTTGA AACGCTTCCC      60

CATAGAATCG CGCTTATTTC AGAAACTTTC TACGCGCCAT CGTTTGGCCT ACGTGGAAGT     120

CGTCAGTAAA TTACCCACGG ATTCGGCGGA GTACCCGGTA CTGGAATATT ATTATCGCTG     180

TCGGTTGATT CAGGATTATA TCAGCGGGAT GACTGACCTT TACGCATGGG ATGAATATCG     240

GCGTTTGATG GCGGTCGAAC AGTAAATGGA CTTTTGTAAA GATGGACAAT AAATTTTTAC     300

TTTTTCCAGA AACTTTATTC CGGAACTTCG CGTTATAAAA TGAATCTGAC GTACACAGCA     360

ATTTTGCGTT ACCTGTTAAT CGAGATTGAA ACAC ATG AAA AAA ACC ACA TTA         412
                                      Met Lys Lys Thr Thr Leu
                                        1               5

GCA ATG AGT GCA CTG GCT CTG AGT TTA GGT TTG GCA TTG TCG CCT CTG       460
Ala Met Ser Ala Leu Ala Leu Ser Leu Gly Leu Ala Leu Ser Pro Leu
            10                  15                  20

TCT GCC ACG GCG GCT GAA ACG TCC TCT TCA GCA ATG ACT GCC CAG CAG       508
Ser Ala Thr Ala Ala Glu Thr Ser Ser Ser Ala Met Thr Ala Gln Gln
        25                  30                  35

ATG CCA AGC CTG GCA CCG ATG CTC GAA AAA GTG ATG CCA TCG GTG GTC       556
Met Pro Ser Leu Ala Pro Met Leu Glu Lys Val Met Pro Ser Val Val
    40                  45                  50

AGT ATT AAT GTT GAA GGT AGC ACC ACG GTG AAT ACG CCG CGT ATG CCG       604
Ser Ile Asn Val Glu Gly Ser Thr Thr Val Asn Thr Pro Arg Met Pro
 55                  60                  65                  70

CGT AAT TTC CAG CAG TTC TTT GGC GAT GAC TCC CCG TTC TGC CAG GAC       652
Arg Asn Phe Gln Gln Phe Phe Gly Asp Asp Ser Pro Phe Cys Gln Asp
                75                  80                  85

GGT TCT CCG TTC CAG AAT TCT CCG TTC TGC CAG GGC GGC GGT AAC GGC       700
Gly Ser Pro Phe Gln Asn Ser Pro Phe Cys Gln Gly Gly Gly Asn Gly
            90                  95                 100

GGC AAC GGC GGT CAA CAA CAG AAA TTC ATG GCG CTG GGC TCC GGC GTA       748
Gly Asn Gly Gly Gln Gln Gln Lys Phe Met Ala Leu Gly Ser Gly Val
       105                 110                 115

ATT ATT GAC GCC GCG AAG GGC TAC GTC GTC ACC AAC AAC CAC GTG GTT       796
Ile Ile Asp Ala Ala Lys Gly Tyr Val Val Thr Asn Asn His Val Val
   120                 125                 130

GAT AAC GCC AGC GTG ATT AAA GTA CAG CTT AGC GAT GGG CGT AAA TTC       844
Asp Asn Ala Ser Val Ile Lys Val Gln Leu Ser Asp Gly Arg Lys Phe
135                 140                 145                 150

GAT GCT AAA GTG GTG GGC AAA GAT CCG CGT TCT GAT ATC GCG CTG ATT       892
Asp Ala Lys Val Val Gly Lys Asp Pro Arg Ser Asp Ile Ala Leu Ile
            155                 160                 165

CAA ATT CAG AAT CCG AAG AAC CTG ACG GCG ATT AAG CTG GCG GAC TCC       940
```

-continued

```
                Gln Ile Gln Asn Pro Lys Asn Leu Thr Ala Ile Lys Leu Ala Asp Ser
                            170                 175                 180

GAC GCG CTG CGC GTG GGG GAT TAT ACC GTC GCT ATT GGT AAC CCG TTT                 988
Asp Ala Leu Arg Val Gly Asp Tyr Thr Val Ala Ile Gly Asn Pro Phe
            185                 190                 195

GGT CTG GGC GAA ACG GTG ACG TCA GGT ATC GTT TCG GCG CTG GGG CGT                1036
Gly Leu Gly Glu Thr Val Thr Ser Gly Ile Val Ser Ala Leu Gly Arg
200                 205                 210

AGC GGC CTG AAC GTA GAA AAT TAC GAG AAC TTT ATT CAG ACC GAC GCC                1084
Ser Gly Leu Asn Val Glu Asn Tyr Glu Asn Phe Ile Gln Thr Asp Ala
215                 220                 225                 230

GCG ATT AAC CGT GGT AAC TCC GGC GGC GCG CTG GTG AAC CTG AAC GGT                1132
Ala Ile Asn Arg Gly Asn Ser Gly Gly Ala Leu Val Asn Leu Asn Gly
            235                 240                 245

GAG CTG ATC GGT ATT AAC ACC GCG ATT CTG GCG CCG GAC GGC GGC AAC                1180
Glu Leu Ile Gly Ile Asn Thr Ala Ile Leu Ala Pro Asp Gly Gly Asn
            250                 255                 260

ATC GGT ATC GGC TTC GCT ATC CCC AGT AAC ATG GTG AAA AAC CTG ACG                1228
Ile Gly Ile Gly Phe Ala Ile Pro Ser Asn Met Val Lys Asn Leu Thr
            265                 270                 275

TCG CAG ATG GTG GAA TAC GGC CAG GTG AAA CGC GGC GAA CTG GGG ATC                1276
Ser Gln Met Val Glu Tyr Gly Gln Val Lys Arg Gly Glu Leu Gly Ile
            280                 285                 290

ATG GGG ACT GAG CTG AAT TCC GAA TTG GCG AAA GCG ATG AAA GTC GAC                1324
Met Gly Thr Glu Leu Asn Ser Glu Leu Ala Lys Ala Met Lys Val Asp
295                 300                 305                 310

GCC CAG CGA GGC GCG TTC GTC AGC CAG GTG ATG CCG AAT TCG TCC GCG                1372
Ala Gln Arg Gly Ala Phe Val Ser Gln Val Met Pro Asn Ser Ser Ala
            315                 320                 325

GCG AAA GCG GGT ATC AAA GCC GGG GAT GTC ATT ACC TCG CTG AAC GGT                1420
Ala Lys Ala Gly Ile Lys Ala Gly Asp Val Ile Thr Ser Leu Asn Gly
            330                 335                 340

AAA CCG ATC AGC AGC TTT GCG GCG CTG CGC GCT CAG GTC GGC ACT ATG                1468
Lys Pro Ile Ser Ser Phe Ala Ala Leu Arg Ala Gln Val Gly Thr Met
            345                 350                 355

CCG GTC GGC AGC AAA ATC AGC CTC GGT CTG CTG CGT GAA GGT AAA GCG                1516
Pro Val Gly Ser Lys Ile Ser Leu Gly Leu Leu Arg Glu Gly Lys Ala
360                 365                 370

ATT ACG GTG AAT CTG GAA CTG CAG CAG AGC AGC CAG AGT CAG GTT GAT                1564
Ile Thr Val Asn Leu Glu Leu Gln Gln Ser Ser Gln Ser Gln Val Asp
375                 380                 385                 390

TCC AGC ACC ATC TTC AGC GGG ATT GAA GGC GCT GAA ATG AGC AAT AAA                1612
Ser Ser Thr Ile Phe Ser Gly Ile Glu Gly Ala Glu Met Ser Asn Lys
            395                 400                 405

GGC CAG GAT AAA GGC GTT GTG GTG AGC AGC GTG AAA GCG AAC TCA CCC                1660
Gly Gln Asp Lys Gly Val Val Val Ser Ser Val Lys Ala Asn Ser Pro
            410                 415                 420

GCC GCG CAA ATT GGC CTC AAA AAA GGC GAT GTG ATT ATC GGC GCT AAC                1708
Ala Ala Gln Ile Gly Leu Lys Lys Gly Asp Val Ile Ile Gly Ala Asn
            425                 430                 435

CAG CAG CCG GTG AAA AAT ATC GCC GAG CTG CGT AAG ATT CTC GAC AGC                1756
Gln Gln Pro Val Lys Asn Ile Ala Glu Leu Arg Lys Ile Leu Asp Ser
            440                 445                 450

AAG CCG TCG GTT CTG GCG CTG AAT ATT CAG CGT GGT GAT AGT TCT ATT                1804
Lys Pro Ser Val Leu Ala Leu Asn Ile Gln Arg Gly Asp Ser Ser Ile
455                 460                 465                 470

TAT TTG CTG ATG CAG TAA TCACCTTTGT CCCCCTTCCG CCATGGAAGG                       1852
Tyr Leu Leu Met Gln *
            475

GGGCAACACT TTTCTGTGAA ACCCCCCACA ACTCCATACT TATTTGCACC GTTTTGTGCA              1912
```

5,980,907

-continued

```
TTTGCACAAT GTCGAGACCT GTCATCTTCC TTATGCTTGT GCTCTGCTCA CAGGAGGGAT    1972

TTATGGCT                                                              1980
```

(2) INFORMATION FOR SEQ ID NO: 2:

(i) SEQUENCE CHARACTERISTICS:
        (A) LENGTH: 475 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Lys Thr Thr Leu Ala Met Ser Ala Leu Ala Leu Ser Leu Gly
 1               5                  10                  15

Leu Ala Leu Ser Pro Leu Ser Ala Thr Ala Ala Glu Thr Ser Ser Ser
                20                  25                  30

Ala Met Thr Ala Gln Gln Met Pro Ser Leu Ala Pro Met Leu Glu Lys
            35                  40                  45

Val Met Pro Ser Val Val Ser Ile Asn Val Glu Gly Ser Thr Thr Val
        50                  55                  60

Asn Thr Pro Arg Met Pro Arg Asn Phe Gln Gln Phe Phe Gly Asp Asp
 65                 70                  75                  80

Ser Pro Phe Cys Gln Asp Gly Ser Pro Phe Gln Asn Ser Pro Phe Cys
                85                  90                  95

Gln Gly Gly Gly Asn Gly Gly Asn Gly Gly Gln Gln Lys Phe Met
                100                 105                 110

Ala Leu Gly Ser Gly Val Ile Ile Asp Ala Ala Lys Gly Tyr Val Val
            115                 120                 125

Thr Asn Asn His Val Val Asp Asn Ala Ser Val Ile Lys Val Gln Leu
        130                 135                 140

Ser Asp Gly Arg Lys Phe Asp Ala Lys Val Val Gly Lys Asp Pro Arg
145                 150                 155                 160

Ser Asp Ile Ala Leu Ile Gln Ile Gln Asn Pro Lys Asn Leu Thr Ala
                165                 170                 175

Ile Lys Leu Ala Asp Ser Asp Ala Leu Arg Val Gly Asp Tyr Thr Val
            180                 185                 190

Ala Ile Gly Asn Pro Phe Gly Leu Gly Glu Thr Val Thr Ser Gly Ile
        195                 200                 205

Val Ser Ala Leu Gly Arg Ser Gly Leu Asn Val Glu Asn Tyr Glu Asn
210                 215                 220

Phe Ile Gln Thr Asp Ala Ala Ile Asn Arg Gly Asn Ser Gly Gly Ala
225                 230                 235                 240

Leu Val Asn Leu Asn Gly Glu Leu Ile Gly Ile Asn Thr Ala Ile Leu
                245                 250                 255

Ala Pro Asp Gly Gly Asn Ile Gly Ile Gly Phe Ala Ile Pro Ser Asn
            260                 265                 270

Met Val Lys Asn Leu Thr Ser Gln Met Val Glu Tyr Gly Gln Val Lys
        275                 280                 285

Arg Gly Glu Leu Gly Ile Met Gly Thr Glu Leu Asn Ser Glu Leu Ala
    290                 295                 300

Lys Ala Met Lys Val Asp Ala Gln Arg Gly Ala Phe Val Ser Gln Val
305                 310                 315                 320

Met Pro Asn Ser Ser Ala Ala Lys Ala Gly Ile Lys Ala Gly Asp Val
                325                 330                 335
```

Ile Thr Ser Leu Asn Gly Lys Pro Ile Ser Ser Phe Ala Ala Leu Arg
            340                 345                 350

Ala Gln Val Gly Thr Met Pro Val Gly Ser Lys Ile Ser Leu Gly Leu
            355                 360                 365

Leu Arg Glu Gly Lys Ala Ile Thr Val Asn Leu Glu Leu Gln Gln Ser
370                 375                 380

Ser Gln Ser Gln Val Asp Ser Ser Thr Ile Phe Ser Gly Ile Glu Gly
385                 390                 395                 400

Ala Glu Met Ser Asn Lys Gly Gln Asp Lys Gly Val Val Ser Ser
            405                 410                 415

Val Lys Ala Asn Ser Pro Ala Ala Gln Ile Gly Leu Lys Lys Gly Asp
            420                 425                 430

Val Ile Ile Gly Ala Asn Gln Gln Pro Val Lys Asn Ile Ala Glu Leu
            435                 440                 445

Arg Lys Ile Leu Asp Ser Lys Pro Ser Val Leu Ala Leu Asn Ile Gln
450                 455                 460

Arg Gly Asp Ser Ser Ile Tyr Leu Leu Met Gln
465                 470                 475

(2) INFORMATION FOR SEQ ID NO: 3:

(i) SEQUENCE CHARACTERISTICS:
        (A) LENGTH: 492 amino acids
        (B) TYPE: amino acid
        (D) TOPOLOGY: linear (ii) MOLECULE TYPE: protein (xi) SEQUENCE DESCRIPTION: SEQ ID NO: 3:

Met Lys Lys Thr Thr Leu Ala Leu Ser Arg Leu Ala Leu Ser Leu Gly
1               5                   10                  15

Leu Ala Leu Ser Pro Leu Ser Ala Thr Ala Ala Glu Thr Ser Ser Ala
            20                  25                  30

Thr Met Thr Ala Gln Gln Met Pro Ser Leu Ala Pro Met Leu Glu Lys
            35                  40                  45

Val Met Pro Ser Val Val Ser Ile Asn Val Glu Gly Ser Thr Thr Val
        50                  55                  60

Asn Thr Pro Arg Met Pro Arg Asn Phe Gln Gln Phe Gly Asp Asp
65                  70                  75                  80

Ser Pro Phe Cys Gln Glu Gly Ser Pro Phe Gln Ser Ser Pro Phe Cys
                85                  90                  95

Gln Gly Gly Gln Gly Gly Asn Gly Gly Gln Gln Gln Lys Phe Met
            100                 105                 110

Ala Leu Gly Ser Gly Val Ile Ile Asp Ala Asp Lys Gly Tyr Val Val
            115                 120                 125

Thr Asn Asn His Val Val Asp Asn Ala Thr Val Ile Lys Val Gln Leu
130                 135                 140

Ser Asp Gly Arg Lys Phe Asp Ala Lys Met Val Gly Lys Asp Pro Arg
145                 150                 155                 160

Ser Asp Ile Ala Leu Ile Gln Ile Gln Asn Pro Lys Asn Leu Thr Ala
                165                 170                 175

Ile Lys Met Ala Asp Ser Asp Ala Leu Arg Val Gly Asp Tyr Thr Val
            180                 185                 190

Gly Ile Gly Asn Pro Phe Gly Leu Gly Glu Thr Val Thr Ser Gly Ile
            195                 200                 205

Val Ser Ala Leu Gly Arg Ser Gly Leu Asn Ala Glu Asn Tyr Glu Asn
            210                 215                 220

```
Phe Ile Gln Thr Asp Ala Ala Ile Asn Arg Gly Asn Ser Gly Gly Ala
225                 230                 235                 240

Leu Val Asn Leu Asn Gly Glu Leu Ile Gly Ile Asn Thr Ala Ile Leu
                245                 250                 255

Ala Pro Asp Gly Gly Asn Ile Gly Ile Gly Phe Ala Ile Pro Ser Asn
                260                 265                 270

Met Val Lys Asn Leu Thr Ser Gln Met Val Glu Tyr Gly Gln Val Lys
            275                 280                 285

Arg Gly Glu Leu Gly Ile Met Gly Thr Glu Leu Asn Ser Glu Leu Ala
            290                 295                 300

Lys Ala Met Lys Val Asp Ala Gln Arg Gly Ala Phe Val Ser Gln Val
305                 310                 315                 320

Leu Pro Asn Ser Ser Ala Ala Lys Ala Gly Ile Lys Ala Gly Asp Val
                325                 330                 335

Ile Thr Ser Leu Asn Gly Lys Pro Ile Ser Ser Phe Ala Ala Leu Arg
                340                 345                 350

Ala Gln Val Gly Thr Met Pro Val Gly Ser Lys Leu Thr Leu Gly Leu
            355                 360                 365

Leu Arg Asp Gly Lys Asn Val Asn Val Asn Leu Glu Leu Gln Gln Ser
    370                 375                 380

Ser Gln Asn Gln Val Asp Ser Ser Ser Ile Phe Asn Gly Ile Glu Gly
385                 390                 395                 400

Ala Glu Met Ser Asn Lys Gly Lys Asp Asn Gly Val Val Val Asn Asn
                405                 410                 415

Val Lys Thr Gly Thr Pro Ala Ala Gln Ile Gly Leu Lys Lys Gly Asp
            420                 425                 430

Val Ile Ile Gly Ala Asn Gln Gln Ala Val Lys Asn Ile Ala Glu Leu
        435                 440                 445

Arg Lys Val Leu Asp Ser Lys Pro Ser Val Leu Ala Leu Asn Ile Gln
    450                 455                 460

Arg Gly Asp Arg His Leu Pro Val Asn Ala Val Ile Ser Leu Asn Pro
465                 470                 475                 480

Phe Leu Lys Thr Gly Arg Gly Ser Pro Tyr Asn Leu
                485                 490
```